United States Patent [19]
Schmidt et al.

[11] Patent Number: 5,393,745
[45] Date of Patent: Feb. 28, 1995

[54] METHOD FOR TREATING APHTHAE USING DIMETHYLPOLYSILOXANE

[76] Inventors: Alfred Schmidt, Leinpfad 2, 22301 Hamburg, Germany; Hans-Jürgen Upmeyer, Mauerkircherstr. 197, 81925 München, Germany

[21] Appl. No.: 207,066

[22] Filed: Mar. 8, 1994

[51] Int. Cl.⁶ .................. A61K 31/695; A61K 31/74
[52] U.S. Cl. .................... 514/63; 424/78.02; 424/78.06; 424/78.07; 424/78.08; 424/49; 514/902; 514/925; 514/928; 514/934
[58] Field of Search ............... 424/78.02, 78.05, 78.06, 424/78.07, 78.08, 49–58, 63; 514/902, 925, 928, 934

[56] References Cited

U.S. PATENT DOCUMENTS

| | | | |
|---|---|---|---|
| 3,507,955 | 4/1970 | Osipow | 424/49 |
| 5,120,533 | 6/1992 | Schmidt et al. | 424/78.08 |
| 5,277,902 | 1/1994 | Schmidt et al. | 424/78.37 |

FOREIGN PATENT DOCUMENTS

| | | |
|---|---|---|
| 302836 | 2/1989 | European Pat. Off. |
| 351301 | 1/1990 | European Pat. Off. |
| 4207704 | 9/1993 | Germany |
| 1194885 | 6/1970 | United Kingdom |
| 90/07930 | 7/1990 | WIPO |
| 90/15591 | 12/1990 | WIPO |
| 91/13608 | 9/1991 | WIPO |

*Primary Examiner*—Shep K. Rose
*Attorney, Agent, or Firm*—Wenderoth, Lind & Ponack

[57] ABSTRACT

The invention disclosed relates to treating aphthae by applying dimeticone to the afflicted oral mucosa.

2 Claims, No Drawings

METHOD FOR TREATING APHTHAE USING DIMETHYLPOLYSILOXANE

TECHNICAL FIELD OF THE INVENTION

This invention relates to methods for treating aphthae.

BACKGROUND OF THE INVENTION

Aphthae are inflammatory changes of the oral mucosa which appear in the form of painful tumefactions of oedematous and infiltrative foci covered with a firmly adhering fibrinous film, and ulcera. These tumefactions are roundish and can become as large as lentil beans. Aphthae have multiple etiology and may be caused by infections and allergic reactions, may ensue from internal diseases, or may be of a psychosomatic nature. Also, acid-containing caustic food may lead to inflammations of the oral mucosa.

A mucosa injury may be the result of a self-inflicted bite.

The therapy of such pathological changes of the oral mucosa depends on the severity of the disease and comprises the treatment of possible primary diseases, the avoidance of mouth-care agents, food or stimulants causing pain, and the topical alleviation of pain by anaesthetic-containing pharmaceuticals, such as Anästhesin TM -containing pharmaceuticals. Moreover, mild, anti-inflammatory washes or corticoid-containing ointments or lozenges are used.

However, there continues to exist a need for a pharmaceutical which is capable of bringing immediate relief from pain and also of prompting the aphthae to heal quickly without, however, inducing possible systemic side effects.

Dimeticone (dimethylpolysiloxane) is at present used to treat flatulence and meteorism. Moreover, the use of dimethylpolysiloxane in the treatment of ulcerous diseases of the stomach and the duodenum and inflammatory diseases of the esophagus and antrum gastritis is known. For instance, WO 90/07930, which is hereby incorporated herein by reference, describes the capability of dimethylpolysiloxane to form and maintain a protective film in the esophagus, the stomach and the duodenum after oral administration. This results in the healing of the afore-mentioned diseases.

SUMMARY OF THE INVENTION

The invention is based on the unexpected finding that the application of dimethylpolysiloxane, in particular of dimeticone-containing solutions onto aphthae leads to an immediate relief from pain, this relief lasting for 3 to 4 hours after application. Moreover, it has been found that the application of a dimethylpolysiloxane liquid three times a day resulted in fast healing of the aphthae. A marked improvement could already be observed after 2 days. Moreover, no undesired side effects were found., Furthermore, dimethylpolysiloxane has a neutral taste and does not have any adverse effects on taste sensation during food intake.

DETAILED DESCRIPTION OF THE INVENTION

Dimethylpolysiloxane may be applied according to the invention in the form of tablets, capsules, patches, emulsions, suspensions and powders for oral administration. It is preferably in liquid form and may be applied together with with a biologically acceptable carrier, such as highly dispersed silicon dioxide, and/or an emulsion, such as an emulsion of water and a salt of a fatty acid (e.g. magnesium stearate). Such compositions may be administered to humans and animals in a safe and effective amount to elicit the desired result. Optionally, the usual flavors, such as peppermint or curled mint fragrant substances, or sweeteners such as Aspartame TM or sodium cyclamate, may be added to the mixture.

Dosage levels and requirements may be chosen by those of ordinary skill in the art from the available methods and techniques. Specific dosage and treatment regimens will depend upon factors such as the severity and course of the aphthae or disposition thereto.

In order that this invention be more fully understood, the following example is set forth. This example is for the purpose of illustration only, and is not to be construed as limiting the scope of the invention in any way.

EXAMPLE

Preparation of treatment composition 100 g of dimethylpolysiloxane, 12 g of highly dispersed silicon dioxide and 100 g of magnesium stearate are melted in a water bath and stirred to form an emulsion. The emulsion is then diluted with water for the preparation of a liquid pharmaceutical which lends itself for administration in the form of drops.

Example of Application

Patient: male

Age: 46

Diagnosis erosions of the oral mucosa (aphthae) showing a whitish fibrinous film;

Cause: unknown; suspected cause: high consumption of citric fruits;

Therapy: application of the dimethylpolysiloxane-containing liquid onto the aphthae 3 times a day;

Effect: The application of the dimethylpolysiloxane-containing liquid brought an immediate relief from pain, which lasted for 3 to 4 hours.

Healing: The application of the dimethylpolysiloxane-containing liquid 3 times a day brought about rapid healing of the aphthae and marked improvement was already recognizable after 2 days. After two more days the erosion was removed.

Side effects: None

Taste: The dimethylpolysiloxane-containing liquid had a neutral taste and did not have any adverse effects on taste sensation during food intake.

While we have described an embodiment of this invention, it is apparent that our embodiment may be altered to provide other embodiments which utilize the method of this invention. Therefore, it will be appreciated that the scope of this invention is to be defined by the appended claims, rather than by the specific embodiment which has been presented by way of example.

We claim:

1. A method for treating aphthae comprising applying an aphthae treating amount of dimethylpolysiloxane in combination with a biologically acceptable carrier to aphthae-afflicted oral mucosa of a human or animal.

2. The method according to claim 1, wherein the dimethylpolysiloxane is applied in the form of an emulsion.

* * * * *

UNITED STATES PATENT AND TRADEMARK OFFICE
CERTIFICATE OF CORRECTION

PATENT NO. : 5,393,745
DATED : February 28, 1995
INVENTOR(S) : Alfred SCHMIDT et al.

It is certified that error appears in the above-indentified patent and that said Letters Patent is hereby corrected as shown below:

On title page, add item [30] insert the following foreign priority data:

--FOREIGN APPLICATION PRIORITY DATA: December 2, 1993 [DE] Federal Republic of Germany P 43 41 139.8--.

Signed and Sealed this

Sixth Day of June, 1995

*Attest:*

BRUCE LEHMAN

*Attesting Officer*     *Commissioner of Patents and Trademarks*